United States Patent [19]
McGill

[11] Patent Number: 5,081,045
[45] Date of Patent: Jan. 14, 1992

[54] CHEMICAL CONCENTRATION PRESSURE ANALYZING APPARATUS AND PROCESS

[76] Inventor: Errol McGill, 3626 Steinhauer Rd., Marietta, Ga. 30066

[21] Appl. No.: 541,042

[22] Filed: Jun. 20, 1990

Related U.S. Application Data

[63] Continuation-in-part of Ser. No. 381,480, Jul. 18, 1989, abandoned.

[51] Int. Cl.⁵ .............................................. G01N 7/18
[52] U.S. Cl. .................................... 436/135; 436/148; 436/177; 422/68.1; 422/80; 422/81; 422/82.13; 73/19.05; 73/31.04
[58] Field of Search ............... 436/135, 136, 148, 177; 73/19.05, 23.2, 31.04; 422/68.1, 78, 80, 81, 82.13, 99, 101

[56] References Cited

U.S. PATENT DOCUMENTS 3,652,223  3/1972  Ludvik .............................. 436/135

Primary Examiner—David L. Lacey
Assistant Examiner—David Redding
Attorney, Agent, or Firm—Bailey & Hardaway

[57] ABSTRACT

An apparatus and method are disclosed for the measurement of hydrogen peroxide concentration from within a textile bleaching bath. The apparatus comprising a sample chamber, a process valve between a source of the solution to be tested and the sample chamber, a reagent valve between a source of reagent and the sample chamber, a pressure measurement tube attached to and extending from the sample chamber, an exhaust valve in communication with the sample chamber, and a pump at a location between the exhaust valve and exhaust device. The process measures hydrogen peroxide concentration by the pressure of the oxygen given off into a known volume as a result of a chemical reaction between the hydrogen peroxide and sodium hypochlorite.

6 Claims, 4 Drawing Sheets

CHEMICAL CONCENTRATION PRESSURE ANALYZING APPARATUS AND PROCESS

BACKGROUND OF THE INVENTION

This patent application is a continuation-in-part of Ser. No. 07/381,480, filed Jul. 18, 1989, now abandoned.

This invention relates generally to the art of chemical analysis and more particularly to the art of detecting the concentration of a specific chemical in solution by pressure analysis.

Cotton, cotton blend and other cellulosic fibers and fabrics are commonly bleached during industrial processing with an alkaline hydrogen peroxide solution. In such a process, the volumetric concentration of hydrogen peroxide must be maintained for successful bleaching. If this concentration deviates from the established norm, the product is unusable. Therefore, variations in hydrogen peroxide concentration can substantially increase overall costs.

The process currently used to test and monitor the hydrogen peroxide concentration is on-line titration. This method has troublesome disadvantages. For example, the remote location of the reaction cell in such systems results in relatively large volumes of solution in the intermediate tubing. Also, the process requires numerous cumbersome steps. On-line titration is, therefore, inefficient. Furthermore, on-line titration is of dubious accuracy. One reason for this dubious accuracy is the active effect of small amounts of contaminants which are frequently insufficiently rinsed from the reaction cell and the intermediate tubing.

Thus, while the above process does monitor the hydrogen peroxide concentration to some degree, no device or process has ever been developed to accomplish this goal in less time, with lower cost and with predictable accuracy.

SUMMARY OF THE INVENTION

It is thus an object of this invention to provide a novel apparatus for detecting the concentration of a particular chemical in solution by pressure analysis.

It is a further object of this invention to provide a novel apparatus for the in situ periodic sampling of a solution and the detection of the concentration of a chemical contained in the solution by pressure analysis.

It is a further object of this invention to provide a novel apparatus for detecting the concentration of a particular chemical in solution by pressure analysis that provides predictable accuracy efficiently and with a minimum of maintenance.

It is also an object of this invention to provide a process for efficiently and quickly measuring the concentration of hydrogen peroxide in a textile bleaching solution.

These as well as other objects are accomplished by an apparatus comprising means defining a sample chamber, a process valve between a source of the solution to be tested and the sample chamber, a reagent valve between a source of reagent and the sample chamber, a pressure measurement tube attached to and extending from the sample chamber, an exhaust valve in communication with the sample chamber, and a pump at a location between the exhaust valve and exhaust means.

The process of this invention is carried out by simultaneously drawing a sample of hydrogen peroxide solution and a predetermined ratio of sodium hypochlorite solution through the sample chamber, capturing a known volume of hydrogen peroxide and sodium hypochlorite solution mixture in the sample chamber, then measuring the pressure resulting from the oxygen gas given off as a product of a chemical reaction between the hydrogen peroxide and the sodium hypochlorite, and, finally, moving air through the filter from the inside of the chamber outwardly to displace the sample and to purge the filter of filtered particles.

DETAILED DESCRIPTION

In accordance with this invention, it has been found that the concentration of a chemical in solution can be measured by pressure analysis when the chemical reacts with a proper reagent. It has further been found that an apparatus mounted in an industrial vessel may be provided to determine the strength of a textile bleaching solution. In the preferred embodiment of the invention, the chemical to be tested will be hydrogen peroxide and the reagent will be sodium hypochlorite. These chemicals will be used for illustration; however, the apparatus of the invention is not intended to be limited to them.

Hydrogen peroxide and sodium hypochlorite react as follows:

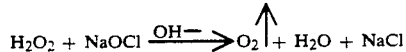

As is apparent from the above equation, one mole of oxygen gas is released when one mole of hydrogen peroxide reacts with one mole of sodium hypochlorite. At STP the oxygen gas will behave ideally and would, therefore, tend to occupy a volume of 22.4 liters. However, if the oxygen gas were confined to a volume X where a vacuum existed prior to the reaction, the pressure in X would increase in accordance with Boyle's Law, which states in an alternative form:

$$P_1 V_1 = P_2 V_2$$

Therefore, $$P_2 = P_1 V_1 / V_2$$

so, $P_2 = (1 \text{ atm}) (22.4 \text{ liters}/X \text{ liters})$
(where $X = V(\text{Total}) - V(H_2O_2 \text{ sol.}) - V(\text{NaOCl sol.})) = 22.4/X$ atm increase in pressure in X As is apparent, the quantity $P_2$ is constant for a particular X. By comparing the pressure measured with $P_2$, the number of moles of gas, and, hence, the number of moles of hydrogen peroxide is evident. The concentration of the hydrogen peroxide solution is then easily obtained. Mathematically, this is expressed as follows:

Moles $O_2 = P/P_2$ where P is the pressure measured
Moles $H_2O_2$ = Moles $O_2$
Then, $$\text{Concentration (\%)} = \frac{(100)(\text{moles } H_2O_2)(34\text{g/mole } H_2O_2)}{(V(H_2O_2 \text{ sol.})\text{liters})(1000\text{g/liter})}$$

Figure 1:
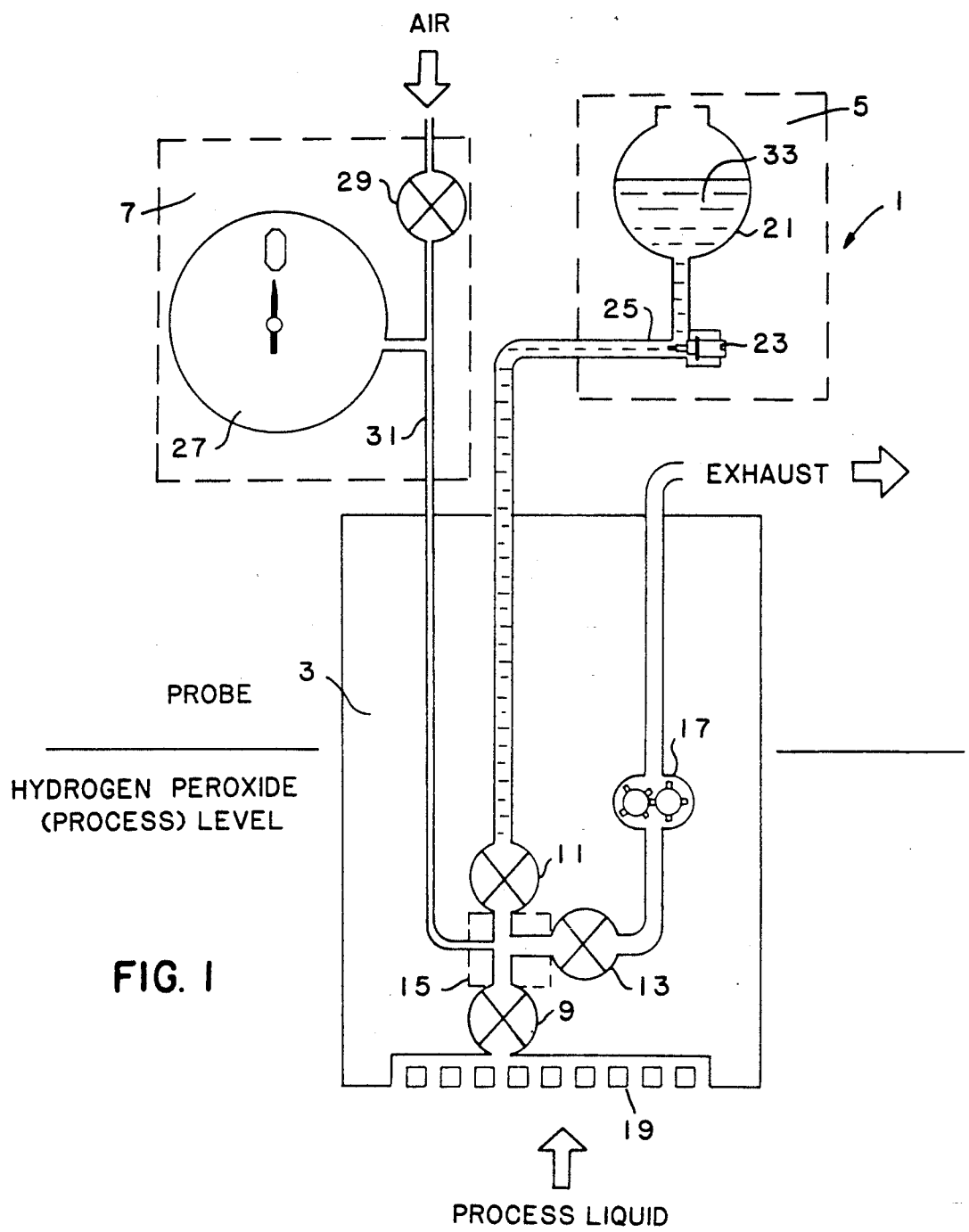
FIG. 1 is a schematic illustration of an apparatus constructed in accordance with the present invention.

FIG. 1 illustrates the apparatus of the preferred embodiment of the invention. The apparatus comprises a chemical concentration pressure analyzer 1. The analyzer 1 can be generally classified by function as having a miniature probe 3, a reagent supply means 5 and pressure measurement/air supply means 7.

Probe 3 comprises:
(a) a process valve 9;
(b) a reagent valve 11;
(c) an exhaust valve 13;
(d) means defining a sample chamber 15;
(e) a pump 17; and,
(f) filter 19.

The reagent supply means 5 comprises:
(a) a reagent supply source, such as reagent tank 21;
(b) a ratio valve 23; and,
(c) a reagent tube 25.

The pressure measurement/air supply means 7 comprises:
(a) pressure measuring means 27;
(b) an air intake valve 29; and,
(c) a pressure measurement tube 31.

Probe 3 is adapted to be mounted in situ submerged within the process solution in a typical industrial processing vessel. As such, process, or hydrogen peroxide, solution will directly enter chamber 15 through filter 19 and process valve 9. Filter 19 filters larger particles from the solution. The distance between the solution and the chamber 15 is consequently only limited by the hardware of the apparatus and is, therefore, very short. This in situ placement provides the apparatus with many of its advantages over the prior art. Furthermore, the volume of chamber 15 is minuscule, typically no greater than three cubic centimeters. The low volume allows quicker mixing than prior art devices, with no need for external mixers. Also, minimum filtration volume resulting from minimum sampling volume is realized.

The sodium hypochlorite solution 33 is drawn by the pump 17 from reagent tank 21 and enters chamber 15 through ration valve 23, reagent tube 25 and reagent valve 11. The ratio valve 23, typically a tapered needle valve, is adjusted to achieve the correct flow rates of hydrogen peroxide and sodium hypochlorite through the system. As a result, the need of the prior art for manual measuring or complex metering is eliminated.

Pressure measuring means 27 measures the pressure in the pressure measurement tube 31, which is connected to chamber 15 and air valve 29. Note that tube 31 extends to a level above the reagent valve 11 and exhaust valve 13. Air valve 29 is also in communication with an air supply source at 35 for filter purging. Pressure measurement/air supply means 7 will typically include visual indication of the measurement and operating status, as shown. Aural warning techniques may be employed as well.

Valve sequencing is provided by electronics. Such methods are well known in the art.

The following hardware has been deemed suitable for the apparatus of the preferred embodiment of the invention:

| 1. Process valve | Kip, Inc. p/n 141022 2-way, normally open solenoid valve |
| --- | --- |
| 2. Exhaust valve | Kip, Inc. Series 1, p/n 141015 2-way, normally closed 12 V solenoid valve |
| 3. Reagent valve | auxiliary h.p. body porting Kip, Inc. p/n 141015 2-way, normally closed 12 V solenoid valve auxiliary bottom metering |
| 4. Air valve | Clippard Instrument Lab., Inc. Model ET-2-12 2-way, normally open 12 V solenoid valve |
| 5. Ratio valve | Lee Instac/LIF p/n TCNA 6201500L 5-turn needle valve |
| 6. Pump | MicroPump Corp. Model 187 with 1/8" npt Face Ports Model 331, 12 V motor |
| 7. Filter | Coors Porcelain Fritted glass filter 75 micron 60 mm. diameter |
| 8. Pressure measurement | Setra Model 280E −14 to 100 psig 4–20 ma |

Figure 2:
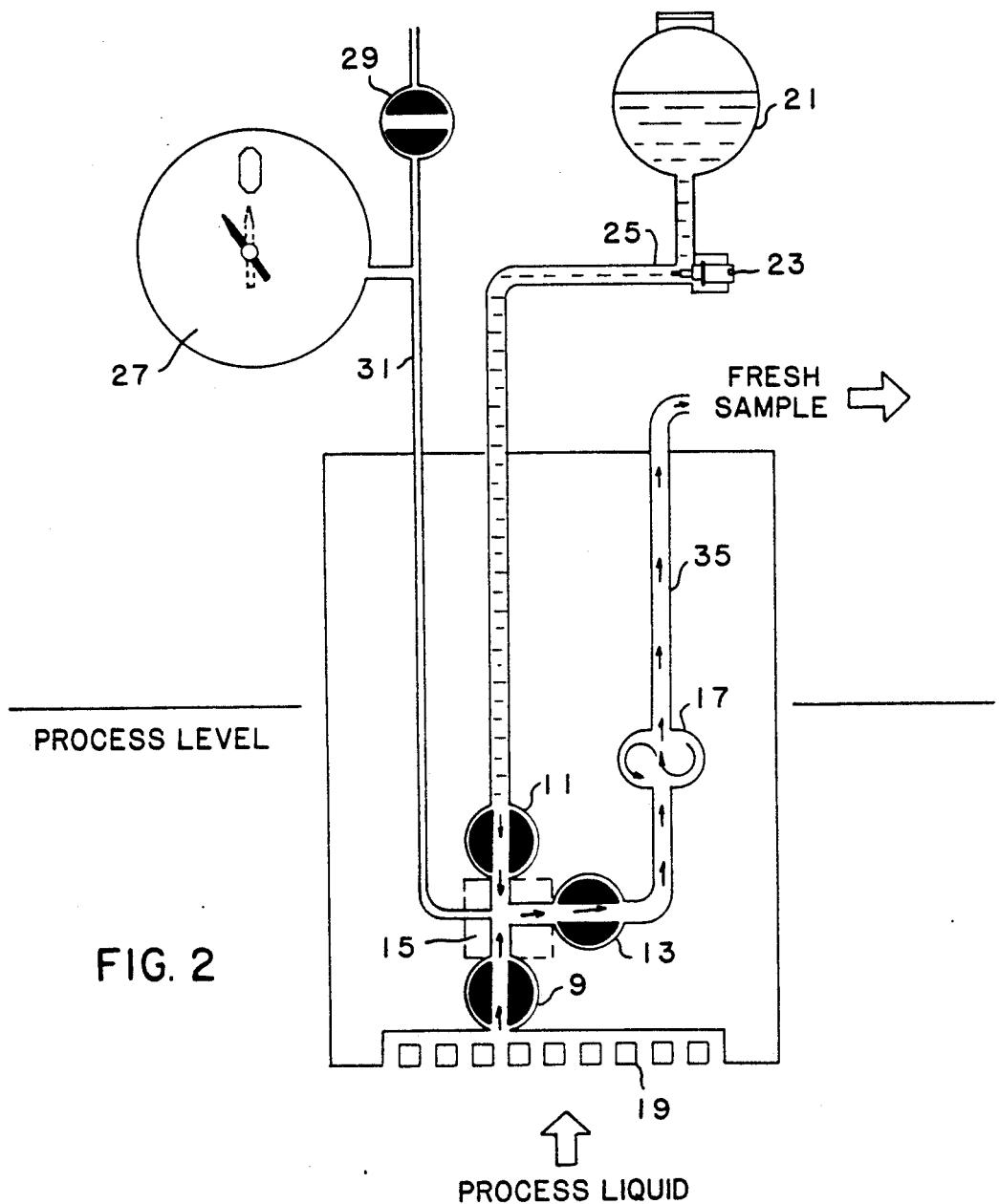
FIGS. 2, 3 and 4 are views similar to FIG. 1 illustrating the sequence of operation.
Figure 3:
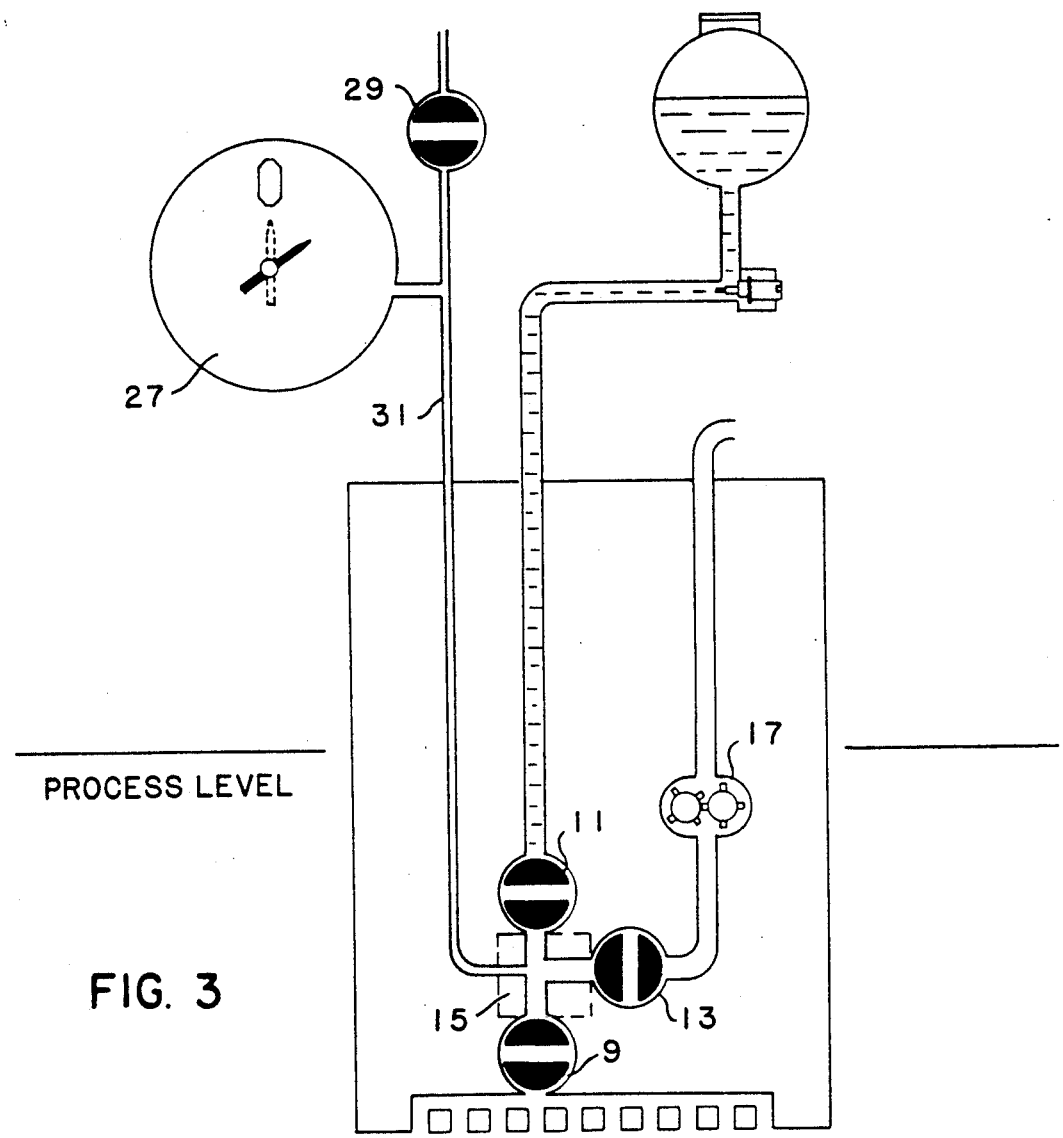

The process of utilizing the apparatus in accordance with the invention is carried out quickly in essentially three steps. The first step, the sample intake, is illustrated in FIG. 2. As is shown, the hydrogen peroxide and sodium hypochlorite solutions are drawn simultaneously through the chamber 15 by pump 17 at flow rates as set by the ratio valve 23. At the same time, residue from the previous sample is displaced through an exhaust means such as exhaust tube 35. The process valve 9, the reagent valve 11 and the exhaust valve 13 are open during this step. The air valve 29 is closed. The pump 17 operates until a steady state is achieved, which occurs in fewer than ten seconds because of the small volume of the chamber 15. FIG. 3 portrays the second step, the pressure measurement. A proportioned mixture of hydrogen peroxide and sodium hypochlorite is entrapped within chamber 15 by the simultaneous closing of the process valve 9, the reagent valve 11, and the exhaust valve 13. The air valve 29 remains closed and the pump 17 turns off. The pumping has left a vacuum of known volume in air tube 31. The hydrogen peroxide and sodium hypochlorite react, giving off oxygen gas. After a short time (less than ten seconds), the reaction is complete and a measurement is taken of the pressure of the oxygen in the former vacuum. If the pressure is too high, the operator can be alerted that the bleaching process should be halted. Alternatively, the bleaching process could be halted automatically. Techniques to automatically halt the bleaching process are well known in the art.

Figure 4:
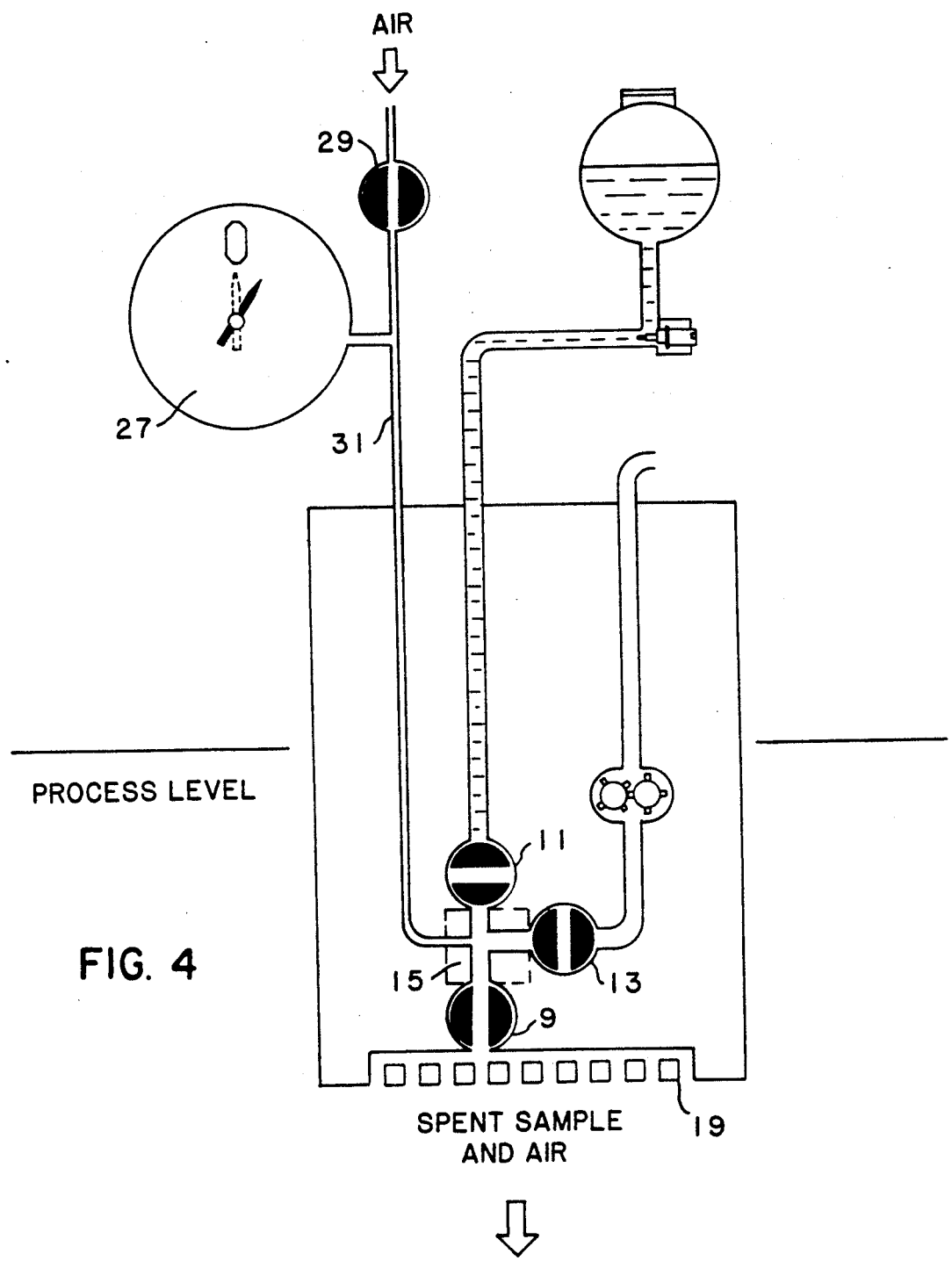

The third step, illustrated in FIG. 4, is the filter clean and purge. During this step the process valve 9 and the air valve 29 are open. The reagent valve 11 and the exhaust valve 13 are closed and the pump 17 is off. Air flow moves through the air valve 29, pressure measurement tube 31, chamber 15 and process valve 9 thereby displacing by pressure the captured mixture through process valve 9 and filter 19. This back-flow of air prevents contaminants from impinging upon the filter 19. As a result, required filter maintenance is reduced and useful filter life is extended. Additionally, the filter back pressure is measured during this step, keeping the operator informed as to the condition of the filter.

It is thus seen that the instant invention provides a novel apparatus for the periodic sampling of a solution and the detection of the concentration of a chemical contained in the solution by pressure analysis. It is further seen that this invention provides a novel process whereby the concentration of hydrogen peroxide in solution can be determined by the pressure of oxygen gas given off as a product in a chemical reaction between hydrogen peroxide and sodium hypochlorite.

The invention accomplishes the unusual combination of accuracy and efficiency. Specifically, some of the advantages over the prior art can be enumerated and summarized as follows:

1. quick cycle time because of low volumes and sample chamber placement;
2. low maintenance because of low volumes, filter back-purging and the need for only one pump; and
3. greater accuracy because:
    (a) the quick cycle time minimizes sample solution destabilization;
    (b) there is no transport of the sample solution to a different temperature zone; and,
    (c) there is no need for multiple accurate small volume measurements of process, reactants, and other chemicals.

As many variations are apparent to one of skill in the art from a reading of the above specification, such variations are within the spirit and scope of the instant invention as defined by the following appended claims.

That which is claimed is:

1. An apparatus for the in situ periodic sampling of a solution for the detection of the concentration of a chemical contained in the solution by pressure analysis, said apparatus comprising:
    means defining a sample chamber;
    a process valve at an end of said sample chamber in flow communication with said sample chamber and a source of the solution to be tested;
    an exhaust valve in flow communication with said sample chamber;
    a pump in flow communication with said exhaust valve and further in flow communication with an exhaust means;
    a reagent valve in flow communication with said sample chamber and a source of reagent;
    a pressure measurement tube attached to and extending from said sample chamber to a point above said reagent valve and said exhaust valve; and,
    means for measuring pressure within said pressure measurement tube;
    whereby said pump operates when said exhaust valve, said process valve and said reagent valve are open to draw reagent and solution previously sampled to said exhaust means while simultaneously drawing new sample solution and reagent into said sample chamber, thereafter said valves are closed and the pressure of gas given off as a product of a reaction between the chemical and the reagent is measured by said measurement means, providing for the determination of the concentration of the chemical in the solution.

2. The apparatus according to claim 1 including a filter positioned and arranged between said process valve and the source of the solution to be tested.

3. The apparatus according to claim 2 wherein said filter is a fritted glass filter.

4. The apparatus of claim 2 further comprising an air supply in communication with said pressure measurement tube and an air valve on said pressure measurement tube regulating flow communication between said sample chamber and said air supply, whereby said filter is purged by opening said process valve and said air valve and, thereafter, pumping air through said filter.

5. The apparatus of claim 1 further comprising a ratio adjustment valve between said reagent valve and said source of reagent whereby the ratio of solution to reagent can be maintained such that the moles of reagent will exceed the moles of the chemical in the solution thereby ensuring that the chemical limits reaction.

6. An analytical process for determining the concentration of a peroxide solution by measuring the pressure of oxygen gas given off when hydrogen peroxide reacts with sodium hypochlorite comprising the steps of:
    drawing a sample of peroxide solution into an elongated sample chamber through a fritted glass filter and simultaneously introducing a predetermined volume of sodium hypochlorite solution as a reagent into the chamber;
    measuring the pressure of oxygen gas given off as a product of a chemical reaction between the hydrogen peroxide and the sodium hypochlorite;
    determining the concentration of peroxide from the pressure of said oxygen given off; and,
    moving air through said filter from the inside of said chamber outwardly to purge said filter of filtered particles and process contaminants.

* * * * *